United States Patent [19]

Pratt

[11] Patent Number: 4,557,842

[45] Date of Patent: Dec. 10, 1985

[54] ALUMINUM SOAP GREASES

[75] Inventor: Charles E. Pratt, Bethlehem, Pa.

[73] Assignee: Joseph Ayers, Inc., Bethlehem, Pa.

[21] Appl. No.: 746,537

[22] Filed: Jun. 19, 1985

Related U.S. Application Data

[63] Continuation-in-part of Ser. No. 519,560, Aug. 2, 1983, Pat. No. 4,525,307.

[51] Int. Cl.$^4$ .......................... C10M 5/12; C10M 7/16
[52] U.S. Cl. .................................. 252/37.7; 556/182; 252/37.5
[58] Field of Search ............................. 252/37.7, 37.5; 556/182

[56] References Cited

U.S. PATENT DOCUMENTS

| | | | |
|---|---|---|---|
| 3,791,972 | 2/1974 | Myers | 252/37.7 |
| 4,132,658 | 1/1979 | Coleman et al. | 252/37.7 |
| 4,280,917 | 7/1981 | Pratt | 252/37.7 |
| 4,303,538 | 12/1981 | Pratt et al. | 252/37.7 |

*Primary Examiner*—Jacqueline V. Howard
*Attorney, Agent, or Firm*—Curtis, Morris & Safford

[57] ABSTRACT

What are disclosed are lubricating greases containing aluminum complex soaps prepared from aluminum isopropoxides modified for stability and improved flash point.

9 Claims, No Drawings

ALUMINUM SOAP GREASES

This application is a continuation-in-part of Ser. No. 519,560 filed Aug. 2, 1983, now U.S. Pat. No. 4,525,307 granted June 25, 1985.

The present invention relates to lubricating greases having improved work stability and thixotropic properties and comprising aluminum complex soaps prepared from modified aluminum isopropoxides having improved properties such as shelf life stability, improved flash point, etc.

BACKGROUND OF THE INVENTION

It is well known that aluminum alkoxide structures are very complex. A summary of these structures, properties, etc., is found in Bradley et al., *Metal Alkoxides*, Academic Press, New York (1978), pages 78 to 81. Moreover, the use of these aluminum alkoxides in paints and coatings is also known, e.g. as discussed in the article published by Turner et al., *The Function of Aluminum Complexes as Structure Modifiers for Paint*, Journal of the Oil and Color Chemists Association, Vol. 41, November 1958, pages 769 et seq.

The production of aluminum alcoholates, i.e. aluminum alkoxides and liquid alkoxides and the like, has also been disclosed in a number of U.S. patents of which the following are known to the inventor: U.S. Pat. No. 2,687,423 issued Aug. 24, 1954 to Mesirow; U.S. Pat. No. 2,845,447 issued July 29, 1958 to Carlson et al.; U.S. Pat. No. 3,006,941 issued Oct. 31, 1961 to Mudrak et al.; U.S. Pat. No. 3,068,263 issued Dec. 11, 1962 to Smith; U.S. Pat. No. 3,305,571 issued Feb. 21, 1967 to Cenker; U.S. Pat. No. 3,920,713 issued Nov. 18, 1975 to Feichtinger et al.; U.S. Pat. No. 4,052,428 issued Oct. 4, 1977 to Lerner et al.; and U.S. Pat. No. 4,132,724 to Turner.

Aluminum alkoxides having the structural formula

are referred to as aluminum tri-alkoxides and are desirable in cases where tri-functionality (i.e. three reactive sites) is desired. The monomeric structure

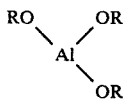

is used for ease of identification, although in actual occurrence there may be two, three, four or more of these aluminum tri-alkoxide molecules joined together by intermolecular forces to form corresponding dimeric, trimeric, tetrameric, or higher polymeric forms of the chemical. An example of the trimeric form of an aluminum tri-alkoxide as proposed in the above mentioned Bradley reference is:

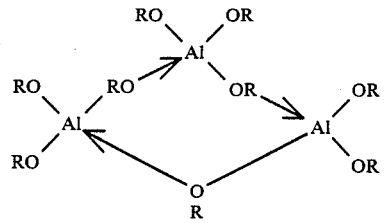

By the same reference, a proposed structure for the tetrameric form of an aluminum tri-alkoxide is:

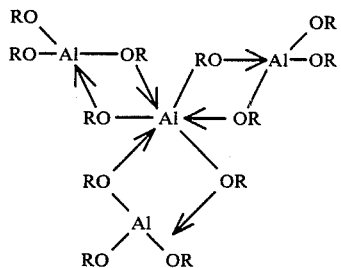

Whether the aluminum tri-alkoxide is in the monomeric, dimeric, trimeric, tetrameric, or higher polymeric form, it is always referred to as tri-functional because there are three reactive OR groups per atom of aluminum.

From the above literature and patent disclosures it is seen that one of the important considerations has been improved stability of the aluminum tri-alkoxides to hydrolysis and to solidification. This stability has been sought to be achieved by introducing acid groups or other reactive groups as replacements for one or more of the OR groups per atom of aluminum. In cases where stabilization is achieved by substituting an acid or other reactant group for one of the OR groups, it can be seen that the functionality of the aluminum compound is thereby reduced.

As discussed in the above mentioned literature references, these aluminum compounds react with moisture, hydroxyl groups, carboxylic acids, carboxyl groups present in other compounds, and carboxylic acid anhydrides. Hence, the usefulness of these compounds has been well established. However, an important commonly available aluminum tri-alkoxide, aluminum tri-isopropoxide, undergoes a physical change from a liquid to a solid during storage. This phenomenon has been described in the above mentioned literature and is explained herein. The polymeric structure of the aluminum isopropoxide is believed to be dimeric, trimeric, or a mixture of both when the product is first made. Upon aging at ambient temperatures, it is generally believed to convert to the tetrameric form, which is a crystalline solid having rather poor solubility characteristics as compared to the freshly made compound in the liquid state.

Thus, aluminum tri-isopropoxide is only commercially available in the form of the solid tetramer, which is usually reduced to a finely divided powder prior to sale and use. Aluminum tri-alkoxides are highly reactive to atmospheric moisture, such reaction greatly reducing the activity of the product. The extremely high surface area of powdered aluminum tri-isopropoxide drastically increases the chance for moisture contact and thereby adversely affects the stability. Also, the solid tetrameric form has poor solubility in aliphatic solvents such as ink oils, and in many cases is only soluble at elevated temperatures.

On the other hand, aluminum tri-secondary butoxide remains liquid in storage at ambient temperatures and is often used in place of aluminum tri-isopropoxide where a tri-functional aluminum alkoxide is desired. However, aluminum tri-secondary butoxide also suffers from a number of serious shortcomings. One of these shortcomings is that the cost of secondary butyl alcohol is higher than that of isopropyl alcohol, making the cost of the aluminum tri-secondary butoxide generally higher than the cost of aluminum tri-isopropoxide. Another serious shortcoming of aluminum tri-secondary butoxide is that it typically has a flash-point lower than 100° F., which property requires it to be shipped and stored as a hazardous "red label" material. Many of the ink and other manufacturing plants desiring to use an aluminum tri-alkoxide are located in areas where the use and/or storage of "red label" materials is prohibited or in areas where insurance premiums would have to be drastically increased if "red label" materials were to be introduced. This "red label" condition of aluminum secondary butoxide can be eliminated by making a very dilute solution of the compound in ink oil solvents having a high boiling point prior to shipment from the plant in which the compound is manufactured. However, this practice increases manufacturing costs and presents an unreasonable increase in freight costs to the customer.

It is obvious that the industry would be greatly benefitted by the development of an aluminum tri-alkoxide that does not suffer from the shortcomings of the prior art. It is the object of this invention to disclose novel aluminum tri-alkoxide compounds which are composed mostly of isopropyl moieties and yet have improved properties with respect to resistance to solidification, increased solubility in hydrocarbon solvents, and also have improved flash point properties.

BRIEF DESCRIPTION OF THE INVENTION

It has now been found that if aluminum tri-isopropoxide is modified by substituting a higher alcohol for isopropyl alcohol in small molar amounts, the reactivity, the stability, and the flash point characteristics of the resulting compound are all improved. Further, when the resulting compound is employed to formulate aluminum complex greases, the resulting greases have improved work stability and a higher degree of thixotropy than do greases formulated with unmodified aluminum tri-isopropoxide, for instance.

The invention is thus predicated in part on the introduction of small molar amounts of an appropriate higher alcohol such that the aluminum content of these compositions is not appreciably reduced. The resulting solvent-free liquids (and even very slightly diluted solutions) are stable for a prolonged period. The outstanding activity of these compounds in inks, for heat set and "quick-set" applications, as well as for coatings, varnishes, paints and the like, makes them very desirable.

These improvements are achieved when the molar amounts of the introduced and reacted alcohol range from about 0.125 to about 0.5 moles per atom of aluminum. A preferred range is from about 0.175 to about 0.45 moles of the alcohol per atom of aluminum and a particularly preferred range is from about 0.25 to about 0.45 moles of alcohol per atom of aluminum.

As modifying alcohols, those having from $C_6$ to $C_{18}$ atoms are useful, with a preferred range being from $C_8$ to $C_{15}$, and a particularly preferred range being from $C_{10}$ to $C_{15}$. Tridecyl alcohol, i.e. $C_{13}H_{28}O$, is the most suitable alcohol. Tridecyl alcohol is commercially available as a mixture predominantly containing $C_{13}$ isomers, most being highly branched, with minor amounts of shorter and longer chain alcohols.

This introduction of appropriate alcohols provides a liquid product having improved solubility characteristics in the hydrocarbon solvents which are compatible with the above recited ink, paint, varnish and like compositions and formulations.

Solvents suitable for use with this invention include the petroleum-derived high-boiling (350°–650° F.) aliphatic hydrocarbon ink oil solvents commercially available under the trademarks "WITSOL" 45 and 50 manufactured by Witco Chemical Co.; the "MAGIE" 400, 470, 520, 620 oils, "MAGIESOL" 40, 44, 47, 52 and 62 manufactured by Magie Bros. Oil Co., as well as lower boiling aliphatic and aromatic hydrocarbon solvents used in paint, varnishes adhesives, and like formulations. The above list of solvents is for illustration only and is not intended exhaustive. Other solvents suitable for use in this invention are the lubricating oil base stocks, both paraffinic and naphthenic, having viscosities at 100° F. ranging from about 35 to 50,000 Saybolt Universal Seconds (SUS).

"WITSOL 45", typical of the ink oil solvents, having a boiling range of about 450° F. to 543° F., has been used herein to study the solubility of these novel compounds and it has been discovered that high solids solutions of these compounds in this solvent have flash points higher than 100° F. This surprising result now makes it possible for industrial consumers to use a liquid tri-alkoxide with a relatively high aluminum content without the attendant danger associated with low flash point prior art compounds.

Storage stability of some of these novel compounds is such that no "red label" precautions are required, thus making available the use of these novel aluminum alkoxides in many heretofore prohibited areas.

As discussed earlier, the low flash point of the prior art compounds and the need to dilute them excessively makes their transportation costs prohibitive. A benefit associated with the present compounds is that the present compounds can be shipped without the excessive dilution required with the prior art compounds.

In addition, the present compounds, being liquid, are easily and readily diluted to give the desired aluminum content in final compositions. For example, for shipping, the compounds are diluted to give solutions containing 50 to 95 percent by weight of the compounds, preferably from 50 to 80 percent by weight.

For the formulation of greases, the compounds of the present invention are converted to aluminum complex soaps by methods known in the art. Such soaps have two carboxylate radicals bound to aluminum, with the third valence of aluminum being satisfied by a hydroxy group. The carboxylate groups may be the same or different and may comprise either aliphatic or aromatic acids, or preferably both.

Thus, according to the present invention, aromatic acids having from 7 to 28 carbon atoms may be employed for formation of the aluminum complex soaps, with benzoic acid being a preferred aromatic acid. Aliphatic acids having from 8 to 40 carbon atoms can be employed for modification of the compounds of the present invention to form soaps, for example stearic acid ₊having 18 carbon atoms, hydrogenated tallow acids which are mostly $C_{18}$ acids with minor amounts of $C_{14}$ and $C_{16}$ acids, fish oils such as arachidic acid having from 20 to 24 carbon atoms. Among these aliphatic acids, those having from 14 to 24 carbon atoms are preferred, preferably those having a major component around $C_{18}$. However, acids which have fewer carbon atoms, down to about $C_8$, are also of interest since they impart particular thioxotropic properties to the oils and greases made therefrom.

Preferably, a mixture of aromatic and aliphatic acids is employed according to the present invention to form aluminum complex soaps from the modified aluminum isopropoxides described. While the ratio of aromatic to aliphatic acids is variable depending on the properties desired in the grease product and on the nature of the oil employed as the base for the grease, generally the molar ratio of aromatic to aliphatic acids is between 0.2:1 and 1.5:1, with a preferred range being from 0.5:1 to 1:1.

The modified aluminum isopropoxides of the invention are converted into aluminum complex soaps by methods known in the art. Generally, one molar part of the aluminum compound is combined in an oil with about 1 to 2.5 molar parts, preferably about 2 molar parts, of the modifying acids at a temperature suitable to melt and dissolve the acids, say about 180° F. The mixture is next heated to a temperature of about 200° F.–225° F. for about one-half hour, with agitation, during which time alkoxy groups are replaced by carboxylate groups. Thereafter, at least one molar part of water is added to promote the liberation of the remaining alcohol from the aluminum compound and the temperature is increased, for example to 310° F.–330° F., and maintained at this temperature for about one hour. Alternatively, the water can be added after the higher temperature has been reached. As the mixture is then cooled, the remainder of the oil to be present in the lubricant is added, together with any additives which may be desired. Suitably, the grease is milled during the cooling step to improve its texture and increase the thickening effect of the aluminum complex soap.

At the temperatures employed in processing, the isopropyl alcohol eliminated from the starting compound of the present invention by replacement with hydroxy and/or carboxylate groups distills off. However, it is not known whether all of the higher alkoxy groups present in the starting materials of the present invention are replaced by acid or water and, to the extent a higher alcohol may be liberated, whether or to what extent the alcohol is removed from the resulting mixture by distillation.

For the formulation of the greases, the oils employed are those commonly used in the prior art, for instance mineral lubricating oil bases, i.e. hydrocarbon oils. They may have a naphthenic base, or may have a paraffin base, or may be a mixed base mineral oil. Other oils which can be thickened according to the present invention are vegetable oils and synthetic oils including both synthetic hydrocarbon base oils, ester-type oils, liquid esters of phosphorous acids, alkylene polymers, polysiloxanes, and the like. The oils employed are those having a viscosity conventional for lubricating purposes.

The aluminum complex soaps according to the present invention are incorporated into an oil in amounts of 1 to 25 percent. Within this range, concentrations of the soap are from 2 to 25 percent give conventional greases, while compositions containing from 1 to 2 percent of the soaps according to the present invention impart interesting thixothropic properties to lubricating oils, i.e., thicken them but not to the stiffness normally associated with a grease. Generally, concentrations of the soap between 5 and 12 percent by weight are preferred. The amount of soap added depends on the properties desired in the final grease, the nature of the soap itself, the thickening efficiency of the soap as affected by working, and the nature of the lubricating oil base.

The manufacture of aluminum complex soaps from aluminum alkoxides and the formulation of the soap into greases is disclosed, for example, in U.S. Pat. Nos. 3,345,291; 3,843,528; and 4,280,917, incorporated herein by reference. The greases prepared according to the present invention have improved working stability in comparison with prior art greases.

A better understanding of the present invention and of its many advantages will be had from the following Examples given by way of illustration.

EXAMPLE 1

7.0 grams of tridecyl alcohol (available from Exxon Chemical Corp.) were added to 20.4 grams of aluminum tri-isopropoxide. The amount added is 0.35 mole per atom of aluminum. The temperature of the mixture was raised to a point where isopropyl alcohol starts distilling off. Heating was continued until the temperature of the mass reached 150° C. and then was held at that temperature for 2 hours. The reaction is an alcohol exchange reaction. The resulting product (an approximate 0.35 mole addition product) is a permanent liquid. This liquid is soluble in ink oil solvents in all proportions. "WITSOL 45", as a typical ink solvent, is used for dilution.

EXAMPLE 2

635.7 grams of aluminum tri-isopropoxide were placed in a 3-necked 2000 ml flash equipped with a stirrer and a heating mantle. The heat was turned on to melt the compound, at which time 109.2 grams of tridecyl alcohol (0.175 mole/atom of Al) were added to the flash. Heating was continued while isopropyl alcohol distills off. The temperature was slowly raised to 150° C. and held between 150° C. and 160° C. for a period of two hours. On cooling, the clear liquid product eventually crystallized to form a heterogeneous mixture of crystals and liquid.

While the above compound was still in a liquid state (prior to crystallization), a portion weighing 271.0 grams was taken from it. 36.5 grams of "WITSOL 45" were added to this portion and the resultant high solids ink oil solution was heated to 200° C. and held at that temperature for 15 minutes. This ink oil solution was then cooled and held for analysis and observation. It was found to contain 9.6% aluminum, was homogeneous and clear, and had improved stability in solvated form, i.e. the solution was still stable after six months.

EXAMPLE 3

3.5 grams tridecyl alcohol were added to 20.4 grams aluminum tri-isopropoxide (0.175 mole per atom of aluminum) and 4.0 grams "WITSOL 45". This mixture was heated and stirred while isopropyl alcohol boiled off. Heating was continued to a temperature of 150° C. and the mass is held at that temperature for a period of two hours. The result was a clear liquid 85.1% dissolved solids solution of the modified aluminum tri-isopropoxide in ink oil solvent. The solution was still stable after six months showing improved solubility of the novel compound.

EXAMPLE 4

418.1 grams of aluminum tri-isopropoxide were added to a 3-necked flask equipped with a stirring motor and a heating mantle. Heat was applied to melt the compound, at which time 145.4 grams of tridecyl alcohol (0.35 mole per atom of aluminum) and 115.5 grams of "WITSOL 45" were added. Heating was continued while isopropyl alcohol boiled off and the temperature slowly rose to 300° F. The temperature is held between 300° F. and 310° F. for 20 minutes and the mixture was then allowed to cool. The resultant product was a permanently liquid high solids solution of the 0.35 molar substituted aluminum composition of this invention. The product was analyzed and found to have an aluminum content of 8.53% and a flash point of 160° F.

8.53% aluminum corresponds with the aluminum content of a 77.8% solids solution of aluminum tri-secondary butoxide. However, aluminum tri-secondary butoxide has a low flash point and requires an ink oil dilution to less than 40% solids content (60% by weight solvent addition) to have a flash point of 100° F. or higher. For comparison it is convenient to reduce both the compound of this invention and aluminum tri-secondary butoxide to an approximately equal aluminum content basis with the same ink oil solvent. The data so obtained are placed for comparison in following Table I:

TABLE I

| Product | Aluminum Assay | Flash Point* |
| --- | --- | --- |
| Compound of Example 4 | 8.53% | 160° F. |
| Aluminum tri-secondary butoxide | 8.57% | 85° F. |
| Compound of Example 4 | 3.64% | 190° F. |
| Aluminum tri-secondary butoxide | 3.70% | 90° F. |

*All flash points are determined according to the method of ASTM-D92, modified to break the surface skin mechanically before each pass of the flame.

EXAMPLE 5

Corresponding substituted compounds were obtained following the procedure as in Example 1 above using decyl alcohol, nonyl alcohol, iso-octyl alcohol, and 2-ethyl-hexanol, adjusting for about equal aluminum content with "WITSOL 45", i.e. about 8.8% Al, and using the alcohol in an amount of 0.35 mole/gram atom of Al, based on the starting isopropoxide compound. All of the above compounds were still clear liquid solutions after five months, indicating improved solubility characteristics over unmodified aluminum tri-isopropoxide. For comparison, unmodified aluminum tri-isopropoxide was diluted to the approximately same aluminum content with the same ink oil solvent, "WITSOL 45", and treated with the same heating profile as the above samples. The unmodified aluminum tri-isopropoxide solution crystallized within one day. For comparative purposes these data are shown below in following Table II:

TABLE II

| Modifying Alcohol | Al Assay (%) | Dissolved Solids (%) | Results |
| --- | --- | --- | --- |
| decyl alcohol | 8.60 | 79.8 | Still clear after 5 months |
| nonyl alcohol | 8.80 | 76.2 | Still clear after 5 months |
| iso-octyl alcohol | 8.85 | 74.6 | Still clear after 5 months |
| 2-ethyl hexanol | 8.88 | 74.5 | Still clear after 5 months |
| unmodified aluminum tri-isopropoxide | 8.80 | 66.6 | Crystalline solid - 1 day |

EXAMPLE 6

Using the same procedure as Example 2, 451.4 grams of aluminum tri-isopropoxide were modified with 110.7 grams of tridecyl alcohol (0.25 mole of alcohol per atom of aluminum). 44.2 grams of "CORAY 22" oil, which is a naphthenic lubricating oil stock having an approximate viscosity at 100° F. of 100 Saybolt Universal Seconds and is a product of Exxon Corp. were added to this compound. The resultant mixture was analyzed and found to contain 10.3% of aluminum and was a lubricating oil solution of a compound of this invention suitable for the manufacture of aluminum complex grease. The product was still a clear solution after 5 months, indicating improved solubility characteristics in lubricating oil stock.

In other, like, applications, the novel compounds show improved characteristics.

While the starting compounds have been illustrated as having a particular polymeric structure, this illustration has been only in aid of understanding the invention. The exact polymeric structures of these compounds are still being questioned; hence, the inventor does not wish to be bound by any theory. However, for the claimed compounds and compositions, the improved characteristics have been established.

Following Examples 7-10 show the compounding of greases according to the present invention employing an aluminum complex soap made from a modified aluminum isopropoxide according to the present invention. Examples 11-14 pertain to the preparation of greases with aluminum complex soaps made from the aluminum isopropoxide of the prior art and Examples 15-17 pertain to greases formulated with a prior art cyclic trimeric aluminum isopropoxide chemically identified as trioxyaluminumtriisopropoxide, commercially available under the trademark "KOLATE 7013".

The modified aluminum isopropylate employed in Examples 7-10 was prepared by adding 171.8 g of iso-octyl alcohol to 771.1 g of aluminum triisopropoxide present in a three-necked 2000 ml flask equipped with a stirrer and heating mantle. The temperature of this mixture was raised to a point where isopropyl alcohol started distilling off. Heating was then continued until the temperature reached 330° F. and was then held at that temperature for 2.5 hours. A vacuum was then applied to the flask to remove the last traces of isopropyl alcohol. In this product, approximately 0.35 mol of isopropoxide per atom of aluminum is replaced by $C_8$ alcohol.

157.5 g of a naphthenic lubricating oil base stock ("CORAY 22") was added to the reaction product. On cooling the product was analyzed and found to have an aluminum content of 10.02% and was liquid at room temperature.

EXAMPLE 7

Formulation of a grease containing 8.0% soap having an acid:aluminum molar ratio of 1.9:1.0 and an aromatic:fatty acid ratio of 0.64:1.0.

318.5 g of a paraffinic base lubricating oil stock having a viscosity of approximately 500 Saybolt Universal Seconds at 100° F. and a viscosity index of 95 ("SUNVIS 150") were placed in a 600 ml stainless steel beaker. 20.8 g of stearic acid having an acid number of 194 and 5.6 g of technical grade benzoic acid were added to this oil. The mixture was heated to raise the temperature to 80° C. to dissolve the acids. 16.6 g of the modified aluminum isopropoxide compound described above were then added and heating was continued with stirring until the temperature reached 150° C. During this heating period, isopropyl alcohol was liberated and distilled off. When the temperature reached 150° C., 2.0 g of water were injected into the mass while vigorous stirring continued. The mass thickened to a grease-like consistency within five minutes while more isopropyl alcohol distilled off. The resulting grease was then allowed to cool and was milled at room temperature with a Morehouse grease mill set at a clearance of 0.005 inch.

In this Example and all following Examples, two batches of the grease were made and penetration values were measured on each batch according to ASTM D-217, 77° F. using a standard penetrometer. Penetration was measured in each case after 60 strokes and again after 10,000 strokes. The samples were then aged for 24 hours and aged penetration tests were performed on the aged samples first with no work and again after 60 strokes. The aged penetration steps were performed with half-sized grease cups and the data were adjusted in known fashion to conform with the aforementioned ASTM. The data contained in these measurements for this Example and the following Examples are tabulated after Example 18.

EXAMPLE 8

Formulation of a grease containing 6.0% soap having an acid:aluminum molar ratio of 1.9:1.0 and an 1.9:1.0 and an aromatic:fatty acid ratio of 0.64:1.0

15.5 g of stearic acid having an acid number of 194 and 4.2 g of technical grade benzoic acid were added to 326.4 g of a solvent extracted paraffinic base lubricating oil stock having a viscosity of approximately 500 SUS at 100° F. and a viscosity index of 65 ("EXXON 1390"). After heating to 80° C., 12.5 g of the modified aluminum isopropoxide mixture earlier described were added and heating was continued until the temperature reached 150° C. Again, at this point, 2.0 g of water were injected into the mass while isopropyl alcohol was liberated and distilled off. After cooling, the grease was again milled and two batches were tested as earlier described.

EXAMPLE 9

Formulation of a grease containing 10.0% soap having an acid:aluminum molar ratio of 1.9:1.0 and an aromatic:fatty acid ratio of 0.85:1.0

24.2 g of stearic acid having an acid number of 194 and 8.6 g of technical grade benzoic acid were dissolved at 80° C. in 310.4 g of the aforementioned "SUNVIS 150" paraffinic base lubricating oil. 21.8 g of the modified aluminum isopropoxide mixture earlier described were added and the mixture was heated and stirred until the temperature reached 150° C. Again, 2.0 g of water were added, the grease was cooled and milled, and the penetration tested.

EXAMPLE 10

Formulation of a grease containing 8.0% soap having an acid:aluminum molar ratio of 1.9:1.0 and an aromatic:fatty acid ratio of 0.85:1.0.

19.3 g of stearic acid and 6.9 g of technical grade benzoic acid were added to 317.7 g of the aforementioned "EXXON 1390" solvent extracted paraffinic base lubricating oil. After heating to 80° C. to dissolve the acids, 17.5 g of the modified aluminum isopropoxide mixture earlier described were added, the temperature was raised to 150° C., water was added, and the mass thickened to a grease consistency within five minutes while liberated isopropyl alcohol was distilled off. After cooling and milling, the penetration properties were measured.

In following Examples 11–14, greases comparable with those of Examples 7–10 are formulated, but employing unmodified aluminum isopropoxide. In each case, formulation of the greases is as before, with addition of stearic and benzoic acids to a base lubricating oil, heating to 80° C., addition of the aluminum compound, heating and stirring to a temperature of 150° C., addition of 2.0 g of water, cooling, milling, and testing.

In each case, the amounts of materials employed are such that Examples 11–14 correlate, respectively, with Examples 7–10. Details are summarized below:

EXAMPLES 11–14

EXAMPLE 11

(8.0% soap; acid:aluminum=1.9:1.0; aromatic:fatty acid=0.64:1.0)

333.4 g of "SUNVIS 150"
20.9 g of stearic acid
5.6 g of benzoic acid
12.6 g of aluminum isopropoxide

EXAMPLE 12

(6.0% soap; acid:aluminum=1.9:1.0; aromatic:fatty acid=0.64:1.0)

337.6 g of "EXXON 1390"
15.5 g stearic acid
4.2 g benzoic acid
9.4 g aluminum isopropoxide

EXAMPLE 13

(10.0% soap; acid:aluminum=1.9:1.0; aromatic:fatty acid=0.85:1.0)

330.0 g of "SUNVIS 150"
24.2 g of stearic acid
8.6 g benzoic acid
16.5 g aluminum isopropoxide

EXAMPLE 14

(8.0% soap; acid:aluminum=1.9:1.0; aromatic:fatty acid=0.85:1.0)

333.5 g of "EXXON 1390"
19.3 g of stearic acid
6.9 g of benzoic acid
13.2 g of aluminum isopropoxide Following Examples 15–18, which correlate respectively with the two prior series of four Examples each, employ the same technique for grease formation, except that the additive is cyclic trioxyaluminumtriisopropoxide. Details are given below:

EXAMPLE 15

(8.0% soap; acid:aluminum=1.9:1.0; aromatic:fatty acid=0.64:1.0)
322.0 g of "SUNVIS 150"
20.8 g of stearic acid
5.6 g of benzoic acid
13.1 g of cyclic trimer ("KOLATE 7013")

EXAMPLE 16

(6.0% soap; acid:aluminum=1.9:1.0; aromatic:fatty acid=0.64:1.0)
329.0 g of "EXXON 1390"
15.6 g of stearic acid
4.2 g of benzoic acid
9.8 g of "KOLATE 7013"

EXAMPLE 17

(10.0% soap; acid:aluminum=1.9:1.0; aromatic:fatty acid=0.85:1.0)
315.0 g of "SUNVIS 150"
24.2 g of stearic acid
8.6 g of benzoic acid
17.2 g of "KOLATE 7013"

EXAMPLE 18

(8.0% soap; acid:aluminum=1.9:1.0; aromatic:fatty acid=0.85:1.0)
322.0 g of "EXXON 1390"
19.3 g of stearic acid
6.9 g of benzoic acid
13.8 g of "KOLATE 7013"

EXAMPLE 19

Formulation of a grease containing 7.0% soap having an acid:aluminum molar ratio of 2.0:1.0 and an aromatic:fatty acid ratio of 0.8:1.0.

17.2 g of stearic acid having an acid number of 194 and 5.8 g of technical grade benzoic acid were dissolved at 80° C. in 325.5 g of di-(2-ethylhexyl)adipate, a compound typical of the di-ester synthetic fluids used as lubricating base stocks. 16.5 g of a modified aluminum isopropoxide compound in a oil stock (described immediately below) were added and the temperature was raised to 150° C. with liberation of isopropyl alcohol. Then, 2.0 g of water were injected into the mass with vigorous stirring. The grease thickened, was allowed to cool, and was milled with a Morehouse grease mill set at a clearance of 0.005 inch.

The grease had a worked penetration of 331, giving it a classification as a No. 1 grease as recognized by the National Lubricating Grease Institute.

The modified aluminum isopropoxide compound used in this example was prepared from 204.2 g of aluminum triisopropoxide and 70.1 g of tridecyl alcohol. Such a mixture was heated until isopropyl alcohol started distilling off and then heating was continued until the mixture reached a temperature of 225° F. This temperature was maintained for a period of 2 hours, whereupon 51.0 g of a mineral oil solvent having a boiling point range of 464° F.-525° F. ("MAGIESOL 47") was added. On cooling, the product was found to have an aluminum content of 8.8% and was liquid at room temperature.

TABLE

| Example No. | 7 | 8 | 9 | 10 | 11 | 12 | 13 | 14 | 15 | 16 | 17 | 18 |
|---|---|---|---|---|---|---|---|---|---|---|---|---|
| Percent Soap | 8.0 | 6.0 | 10.0 | 8.0 | 8.0 | 6.0 | 10.0 | 8.0 | 8.0 | 6.0 | 10.0 | 8.0 |
| Benzoic/Stearic Ratio | 0.64 | 0.64 | 0.85 | 0.85 | 0.64 | 0.64 | 0.85 | 0.85 | 0.64 | 0.64 | 0.85 | 0.85 |
| TESTS | | | | | | | | | | | | |
| Penetration 60 Strokes | 288 | 326 | 291 | 294 | 283 | 290 | 258 | 265 | 273 | 290 | 293 | 269 |
| Penetration 10,000 Strokes | 295 | 330 | 288 | 297 | 312 | 316 | 310 | 310 | 298 | 305 | 317 | 293 |
| Percent Change | 2.4 | 1.2 | 1.0 | 1.0 | 10.2 | 9.0 | 20.2 | 17.0 | 9.2 | 5.2 | 8.2 | 8.9 |
| Aged Pen. 24 hrs. (not worked) | 204 | 239 | 214 | 221 | 255 | 255 | 263 | 261 | 243 | 242 | 266 | 273 |
| % Change (from 10,000 strokes) | 30.8 | 27.6 | 25.7 | 25.6 | 18.3 | 19.3 | 15.2 | 15.8 | 18.5 | 20.7 | 16.1 | 6.8 |
| Aged Pen. 24 hrs. (60 strokes) | 293 | 327 | 298 | 296 | 328 | 317 | 318 | 309 | 305 | 315 | 321 | 301 |
| % Change (from 10,000 strokes) | 0.7 | 0.9 | 3.5 | 0.3 | 5.1 | 0.3 | 2.6 | 0.3 | 2.3 | 3.3 | 1.3 | 2.7 |

It is evident from the penetration values at 60 strokes and 10,000 strokes given in the Table that the change in viscosity in the greases prepared according to the present invention is lower on working than is the change observed in the prior art samples after a similar degree of working.

From the data obtained on the aged samples which were not worked, it will be noted that in every case the viscosity increases on standing, a phenomena known as "setback". The "setback" in the compositions of the present invention is slightly greater than the compositions of the prior art, indicative of the thixotropic rheology of the greases made according to the present invention.

Finally, the data relating to penetration on aged samples after 60 strokes show that the samples of the invention revert to substantially their original viscosity values, again establishing the thixotropy of the greases according to the present invention.

What is claimed is:

1. A lubricating grease containing an aluminum complex soap prepared by reacting (1) one molar part of a modified aluminum isopropoxide wherein about 0.125 to about 0.50 mole of isopropoxide, per atom of aluminum, is replaced with an alkoxide of a $C_6$- to $C_{18}$- alcohol, with (2) from 1 to 2.5 molar parts of a mixture of a $C_7$-$C_{28}$ aromatic acid and a $C_8$-$C_{28}$ aliphatic acid wherein the molar ratio of aromatic to aliphatic acid is between 0.2:1 and 1.5:1, in a lubricating oil base stock, and then reacting this product with (3) water.

2. A grease as in claim 1 wherein said lubricating oil base stock is a petroleum derived hydrocarbon or a synthetic oil.

3. A grease as in claim 1 containing from 1 to 25 percent by weight of said aluminum complex soap.

4. A grease as in claim 3 containing at least 2 percent by weight of said aluminum complex soap.

5. A grease as in claim 1 wherein said molar ratio of aromatic to aliphatic acids is between 0.2:1 and 1.5:1.

6. A grease as in claim 1 wherein said aromatic acid is benzoic acid.

7. A grease as in claim 1 wherein said aliphatic acid is at least one $C_{14}$- to $C_{24}$- aliphatic acid.

8. A grease as in claim 7 wherein said aliphatic acid is a $C_{18}$- acid or a mixture of acids containing a major amount of $C_{18}$- acid.

9. A grease as in claim 7 wherein said acid is stearic acid.

* * * * *